United States Patent [19]

Rao

[11] Patent Number: 5,380,916
[45] Date of Patent: Jan. 10, 1995

[54] METHOD FOR THE ISOLATION AND PURIFICATION OF TAXANE DERIVATIVES

[75] Inventor: Koppaka V. Rao, Gainesville, Fla.

[73] Assignee: University of Florida, Gainesville, Fla.

[21] Appl. No.: 915,736

[22] PCT Filed: Nov. 4, 1901

[86] PCT No.: PCT/US91/08189

§ 371 Date: Jul. 16, 1992

§ 102(e) Date: Jul. 16, 1992

Related U.S. Application Data

[63] Continuation-in-part of Ser. No. 611,109, Nov. 2, 1990, abandoned.

[51] Int. Cl.$^6$ .............................................. C07C 69/76
[52] U.S. Cl. ...................... 560/107; 549/510
[58] Field of Search ............... 560/107, 106; 549/510

[56] References Cited

U.S. PATENT DOCUMENTS

| | | | |
|---|---|---|---|
| Re. 34,277 | 6/1993 | Denis et al. | 549/510 |
| 4,206,221 | 6/1980 | Miller et al. | 424/278 |
| 4,814,470 | 3/1989 | Colin et al. | 514/449 |
| 4,876,399 | 10/1989 | Holton et al. | 568/817 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,175,315 | 12/1992 | Holton | 549/510 |
| 5,194,635 | 3/1993 | Kingston et al. | 549/430 |
| 5,200,534 | 4/1993 | Rao | 549/510 |
| 5,202,448 | 4/1993 | Carver et al. | 549/510 |

OTHER PUBLICATIONS

Miller Roger W., Journal of Natural Products, vol. 43(4) p. 425t, 1980 (II).

Witherup et al, Journal of Liquid Chromatography, 12 (11), 2117–2132 1989.

Miller, Roger W., Richard G. Powell, and Cecil R. Smith, Jr. (1981) "Antileukemic Alkaloids from *Taxus wallichiana* Zucc," J. Org. Chem. 46(7):1469–1474 (I).

Kingston, David G., Douglas R. Hawkins, and Liza Ovington (1982) "New Taxanes from *Taxus brevifolia*" Journal of Natural Products 45(4): 466–470.

Wani, M. C., H. L. Taylor, Monroe E. Wall (1971) "Plant Antitumor Agents. VI. The Isolation and Sturcture of Taxol, a Novel Antileukemic and Antitumor Agent from *Taxus brevifolia*" Journal of the American Chemical Society 93(9):2325–2327.

McLaughlin, Jerry L., Roger W. Miller, Richard G. Powell, and Cecil R. Smith, Jr. (1981) "19-Hydroxybaccatin III, 10–Deacetylcephalo–Mannine, and 10–Deacetyltaxol: New Antitumor Taxanes from *Taxus wallichiana*" Journal of Natural Products 44(3):312–319.

Huang, D. H. Oliver, David G. I. Kingston, Neal F. Magri, G. Samaranayake (1986)"New Taxanes from *Taxus brevifolia*" Journal of Natural Products 49(4);665–669.

*Primary Examiner*—Glennon H. Hollrah
*Assistant Examiner*—Deborah Lambrin
*Attorney, Agent, or Firm*—Saliwanchik & Saliwanchik

[57] ABSTRACT

An improved method for isolating certain clinically important taxane derivatives from the crude extract of a naturally occurring Taxus species comprising treating the extract by reverse phase liquid chromatography on an adsorbent; causing the taxane derivatives to be adsorbed on the adsorbent; and recovering the taxane derivatives from the adsorbent by elution with an elutant. The taxane derivatives thus isolated in pure form are taxol, taxol-7-xyloside, 10-deacetyitaxol, 10-deacetyltaxol-7-xyloside, cephalomannine, cephalomannine-7-xyloside, 10-deactylcephalomannine-7-xyloside, baccatin III, 10-deacetylbaccatin III, baccatin VI, and brevitaxane A.

1 Claim, 3 Drawing Sheets

METHOD FOR THE ISOLATION AND PURIFICATION OF TAXANE DERIVATIVES

This application is a continuation-in-part of U.S. patent application Ser. No. 07/611,109 filed Nov. 2, 1990 now abandoned.

BACKGROUND OF THE INVENTION

1. Field of the Invention

This invention relates to the isolation and purification of taxane derivatives from a naturally occurring Taxus species, and more particularly, to an improved method for isolating taxol and the congeners thereof from the Taxus species by reverse phase liquid chromatography.

2. Related Art

Taxol was first isolated in 1971 from the western yew, *Taxus brevifolia* by Wani, et al. (J. Am. Chem. Soc., 93:2325, 1971), who characterized its structure by chemical and X-ray crystallographic methods.

Taxol is a member of the taxane family of diterpenes having the following structure:

Taxol and various taxane derivatives including cephalomannine are highly cytotoxic and possess strong in vivo activities in a number of leukemic and tumor systems. Especially, taxol is considered an exceptionally promising cancer chemotherapeutic agent, and is currently in phase II clinical trials in the United States. However, the major problem with the ongoing clinical trial is the limited availability of the compound.

The only available natural source for taxol so far is several species of very slowgrowing yew (genus Taxus, family Taxaceae). The isolation procedures currently practiced are very difficult, low-yielding, and obviously fatal to the source. For example, C. H. O. Huang et al. (J. Nat. Prod., 49, 665, 1986) reported a 0.01% yield from a large scale isolation starting with 806 lbs. or more of *Taxus brevifolia* bark. According to Huang's method, the ground bark is extracted with methanol. The methanol extract is concentrated and the concentrate extracted with dichloromethane. The dichloromethane extract is then concentrated and the concentrate is dispersed in 1:1 acetone-hexane. The soluble portion is applied to a column of Florisil in hexane/acetone and then eluted with hexane containing an increasing amount of acetone (30%–50%). The taxol-containing fractions are collected and concentrated to obtain a crude composition containing taxol. The taxol in the crude composition is recrystallized once from methanol-water and a second time from hexane-acetone. The recrystallized taxol is further purified by chromatography on silica gel and recrystallized again. All the mother liquors are combined, recrystallized, and chromatographed to yield additional quantities of purified taxol. The isolation of taxol was described by other workers: R. W. Miller, et al., J. Org. Chem., 46, 1469, 1981; J. L. McLaughlin, et al., J. Nat. Prod., 44, 312, 1981; D. G. I. Kingston, et al., J. Nat. Prod., 45, 466, 1982; and V. Senih, et al., J. Nat. Prod., 47, 131, 194. The reported yields of taxol from various species of yew range from 50 mg/kg to 165 mg/kg (i.e., 0.005–0.017%).

In view of the high therapeutic potential of taxol, the synthesis of the compound has attracted much interest among synthetic organic chemists worldwide. Disappointedly, the synthesis of a natural product with such complexity, however, appears to be of little practical value.

Because of the current state of synthetic efforts, the isolation of taxol from Taxus species, despite low yields, will be the only reliable supply source for clinical quantities of taxol for years to come. Thus, purification techniques which provide higher yields of taxol are needed to provide greater quantities of this promising therapeutic agent. The present invention provides a purification technique which accomplishes this goal.

SUMMARY OF THE INVENTION

In view of the foregoing, it is a primary objective of this invention to provide an improved method for the isolation of taxol and the congeners thereof from a Taxus species.

It has now surprisingly been found that taxol and the congeners thereof can be isolated and purified from *Taxus brevifolia* and other Taxus species in high yields by reverse phase liquid chromatography. Some of the other isolated taxane derivatives such as 10-deacetyltaxol-7-xyloside, taxol-7-xyloside, 10-deacetylbaccatin III, and 10-deacetyltaxol could also be converted to taxol by chemical synthesis.

According to this invention, there is provided a method for isolating a taxane derivative from the crude extract of a naturally occurring Taxus species comprising the steps of:

(a) treating the crude extract by reverse phase liquid chromatography on an adsorbent and causing the taxane derivative to be adsorbed on the adsorbent; and (b) eluting the taxane derivative from the adsorbent; and (c) recovering the taxane derivative.

These and other objectives, as well as the nature, scope, and utilization of this invention, will become readily apparent to those skilled in the art from the following description, the drawings and the appended claims.

DETAILED DESCRIPTION OF THE INVENTION

Taxane derivatives isolated and purified in accordance with this invention are characterized by the following chemical structure:

Taxol, wherein $R_3 = H$

Taxol-7-xyloside, wherein $R_3 =$ xylosyl

10-Deacetyltaxol-7-xyloside, wherein $R_3 =$ xylosyl

Cephalomannine, wherein $R_3 = H$

Cephalomannine-7-xyloside, wherein

$R_3 =$ xylosyl

10-Deacctylcephalomannine-7-xyloside, wherein

$R_3 =$ xylosyl

Baccatin III, wherein
     $R_3 = H$

10-Deacetylbaccatin III, wherein
     $R_3 = H$

Baccatin VI

Brevitaxane-A

The staring material for use in this invention is a plant material selected from the group of plants commonly referred to as taxads. The most suitable plants of this group are species of Taxus. Among Taxus species, *Taxus brevifolia* is particularly preferred. Also, the preferred plant source is *Taxus floridana*. While it is convenient to use certain parts of the Taxus tree in this invention, the taxane derivatives can be extracted from the whole plant or from separated parts such as wood, stems, roots, leaves (needles), seeds, or mixtures thereof. The material to be extracted can be either fresh or dried. Preferably, the bark or the needles are used. Further, the method of this invention can be used to purify taxanes from plant cells grown, or culture supernatants obtained by using in vitro culture technology. Additionally, the method is applicable to the separation and purification of taxanes from taxane mixtures treated by conventional chromatographic techniques. The method can be further applied to the separation and purification of taxanes from the semisynthesis or total synthesis of taxol and its analogues.

Figure 1:
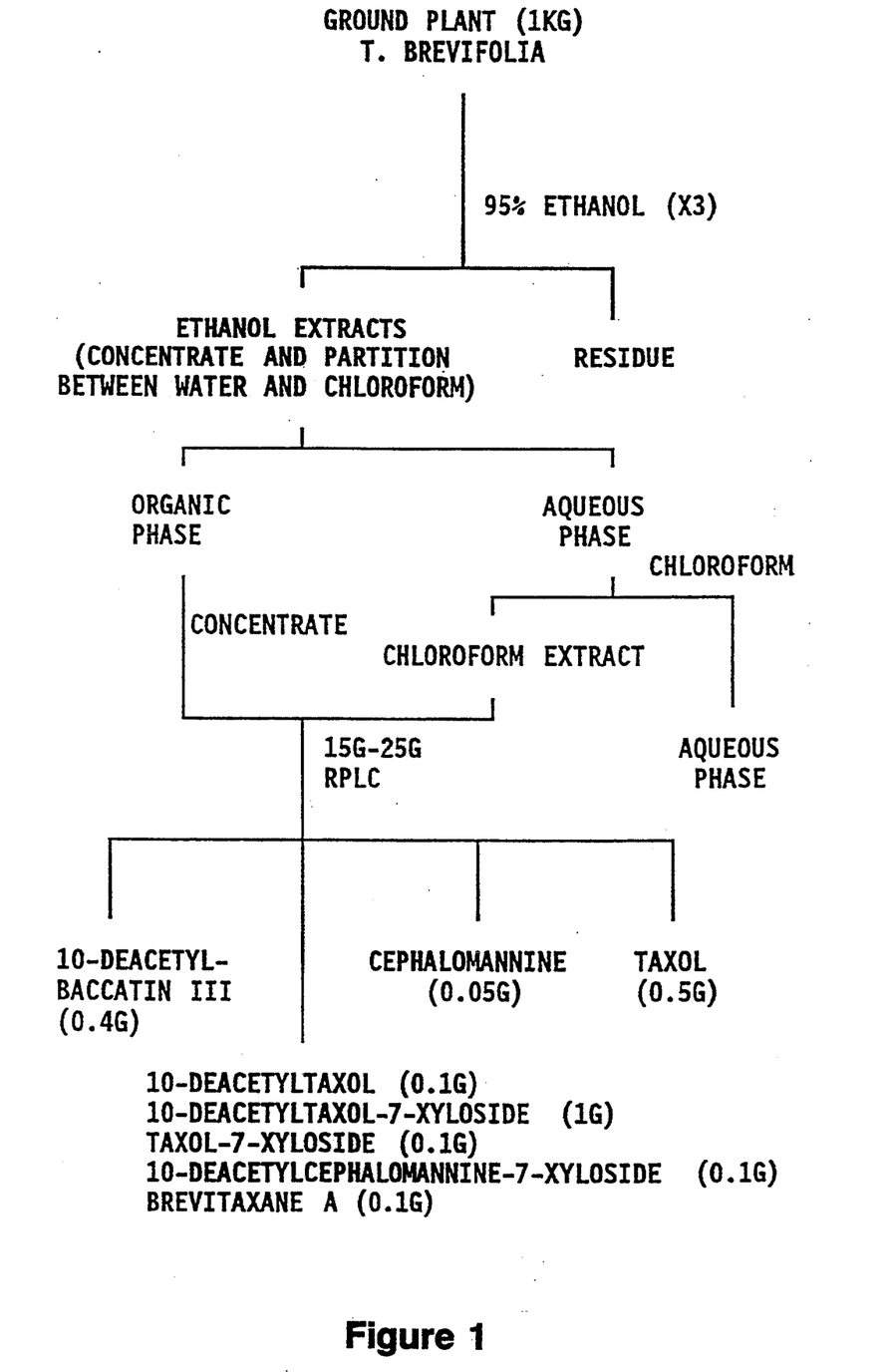
FIG. 1 shows a separation scheme for isolating taxanes from *Taxus brevifolia* in accordance with this invention.

The plant material is first dried and ground to a suitable particle size usually ranging from about 0.001 to about 10 $mm^3$. This may be accomplished by serial passage through a chipper and a conventional grinding mill. The ground material is then extracted with a polar solvent such as an alcohol, preferably 95% ethanol or methanol. The extraction normally continues to 24 hours at ambient temperature. The solvent extract is concentrated at reduced pressure to approximately 5% of its original volume. The concentrated extract of the ground plant material (0.1 g to 1 kg) is processed in a solvent-partitioning scheme, such as shown in FIG. 1, in FIG. 2, or in FIG. 3. The concentrate is thus partitioned between two immiscible solvents, preferably a water-chloroform or water-dichloromethane mixture. Other representative solvents suitable for the partition process include 1,2-dichloroethane, 1,1-dichloromethane, 1,1-dichloroethane, benzene, toluene, methyl isobutyl ketone, and amyl acetate. After equilibration, the organic phase is separated and the aqueous phase is extracted with the organic solvent for several times. The combined organic phase is concentrated at reduced pressure to dryness. The mass obtained constitutes a crude taxane extract substantially free from the extraction solvent. Different forms of the crude extract result, such as a solid, syrup or a gummy semisolid, depending on the extraction conditions used. The term "crude taxane extract" used herein means an extract which has not substantially been purified by conventional column chromatographic techniques or any other equivalent purification methods.

In accordance with this invention, the crude taxane extract is subjected to reverse phase liquid chromatography ("RPLC") in order to separate taxane derivatives contained in the extract and to isolate each derivative in pure form. Several variables are usually examined to achieve separation and purification by liquid chromatography: column packing (stationary phase or adsorbent), composition of an elutant (mobile phase), column dimension, and elutant flow rate.

When practicing this invention, silica gel based reverse phase particles are particularly suitable as the adsorbent. Preferably, hydrocarbon-bonded silica gel having $C_8$ to $C_{18}$ alkyl groups, cyano-bonded silica gel, or phenylalkyl-bonded silica gel is used. Especially preferred is $C_8$ to $C_{18}$ bonded silica gel. Particularly preferred are $C_8$ bonded silica gel and $C_{18}$ bonded silica gel.

A noteworthy feature of this invention is the preferred use of a single column in chromatography. This single column technique accomplishes the separation of taxanes from the crude extract, affording crystalline solids from which purified taxanes are obtained by recrystallization. Such efficient separation by a single column is totally unexpected and is contrary to the belief of those skilled in the art that the taxol separation process always requires a multi-column system.

Solvents (elutant) useful in this invention can be selected by reference to the standard practices of chromatography. A polar elutant, such as lower alcohol, acetone, acetic acid, and acetonitrile is normally employed when the adsorbent has low polarity. A water-miscible organic solvent, such as acetonitrile or methanol, in water is preferably used as the elutant. An acetonitrile-water mixture with acetonitrile being in the range of from 0% to 100% is conveniently employed.

The concentration limits of the gradients are determined by the concentration of organic solvent necessary to elute taxanes from the adsorbent and the requirement that the organic solvent be completely miscible and exist in a single phase at the concentration required to elute the taxanes. Initially, a concentration of 10–40% acetonitrile is used and is increased as separation and purification progresses. Other solvents with broad water-miscibility properties similar to those of acetonitrile are also suitable, e.g., straight or branched chain alkanols containing from 2 to 6 carbons including, but not limited to, ethanol, n-propanol, isopropanol, n-butanol, and hexanol. Lower aliphatic ketones such as acetone, methyl ethyl ketone, and diethyl ketone, cyclic ethers such as tetrahydrofuran and dioxane, dimethyl formamide, esters such as methyl and ethyl acetates, and dimethyl sulfoxide can also be used without adverse effects on separation. These solvents and others are used alone or in combination with acetonitrile.

The chromatographic column dimensions, and the temperature, flow rates, and time of chromatographic separations are not critical to the practice of this invention, and are based primarily upon the requirements for efficient chromatography which are known to those of skill in the art or can be readily determined without undue experimentation.

The liquid chromatography systems of this invention may be used in either preparative or analytical modes. Preparative columns require larger load capacity, and typically are 13–150 mm O.D.×300–1800 mm long. In contrast, analytical columns are smaller, typically 4.6 mm O.D.×300 mm long. Those skilled in the art of chromatography will, without undue experimentation, select chromatographic bed dimensions (i.e., the particle size of a adsorbent material) appropriate to the amounts of materials being separated.

Flow rates of elutant are adjusted based on such factors as the column dimensions; the degree of peak resolution desired; the particle size of the stationary phase; and the time required to achieve satisfactory peak resolution. For example, analytical columns use slower flow rates, typically 0.1 ml–5ml/minute, whereas preparative columns use faster flow rates, typically 10 ml to several hundred ml/minute. The times required for chromatographic runs range from about 10 minutes to about 30 hours. Temperatures for chromatographic separation are typically at ambient temperatures, although slightly higher temperatures may be used.

When practicing the chromatographic separation of this invention, either a HPLC mode, which operates at high pressures (500–2000 psi), or a MPLC mode, which operates at medium pressures (100–500 psi), or a LPLC mode, which operates at low pressures (10–100 psi), is employed.

Having described specific chromatographic techniques and conditions suitable for this invention, a preferred embodiment of the isolation, separation, and purification of the taxanes derivatives in accordance with this invention follows. The crude solvent extract of the taxane derivatives is subjected to reverse phase column chromatography using the separation conditions as set forth above. This procedure affords a series of fractions which are found to contain a more polar compound, namely 10-deacetylbaccatin III. A second stage of column chromatography gives a new series of fractions which contains 10-deacetyltaxol-7-xyloside, 10-deacetylcephalomannine-7-xyloside, taxol-7-xyloside, 10-deacetyltaxol brevitaxane A, cephalomannine, and taxol in this order of eluting sequence. Taxol can conveniently be recrystallized from respective fractions rich in these components and other taxanes. Recrystallization may be carried out by standard techniques known in the art. Although a variety of common organic solvents can be used, a water miscible solvent in water, such as methanol/water or acetonitrile/water, is preferred. Other representative solvents include chloroform, benzene, ethyl acetate, ether, and acetone. These solvents are normally used in combination with a non-polar solvent such as ligroin or n-pentane. The mother liquors from the recrystallization are combined with fractions less rich in taxol, and are subjected to chromatography again using the same separation conditions as those used for the first separation. Likewise, other taxanes can be chromatographically processed. An adsorbent different from that used for the first separation may be employed in RPLC. After recrystallization, a combined yield of taxol is obtained. Similarly, cephalomannine is isolated and purified by recrystallization.

The more polar fractions may be, likewise, chromatographed to separate 10-deacetylbaccatin III, although the compound either crystallizes out directly from the fractions or can be crystallized upon concentration of the fractions. Alternatively, this second chromatography on the reverse stationary phase can be substituted by standard chromatography using a silica gel column or a Florisil column or even an alumina column. The taxane derivatives can be recrystallized from the same solvent combinations as set forth above, affording pure natural products.

In accordance with another preferred embodiment of this invention, the concentrated extract of the needles (fresh or dried) of the Taxus plant is processed in a slightly different manner from that used for the bark extract. Thus, the needle extract is partitioned between aqueous methanol and ligroin. The ligroin phase takes up undesirable lipid components including chlorophylls, carotenoids, oils, and the like. The aqueous methanol phase is extracted successively using suitable organic solvents with different polarities. The less polar extract mainly contains taxol, and the more polar extract 10-deacetylbaccatin III, with brevitaxane A in both extracts. Both extracts are separately subjected to RPLC using substantially the same separation conditions as those described previously. Early fractions from the two separations are combined and concentrated to yield 10-deacetylbaccatin III. Later fractions are combined and concentrated to yield brevitaxane A, cephalomannine and taxol. After fractional separation, all the taxanes can be isolated and recrystallized. For an additional chromatography (rechromatography), a silica gel column or a Florisil column or an alumina column may be employed in lieu of a reverse phase column, if desired. Alternatively, the aqueous methanol phase after the ligroin partition is extracted with a single solvent such as chloroform. The taxane extract is then chromatographed on a reverse phase column to separate 10-deacetylbaccatin III, brevitaxane A, cephalomannine, and taxol, respectively, from each other. Each taxane can be isolated and recrystallized as previously described.

Alternatively, a needle methanol extract in concentrated form is partitioned between water and chloroform. The chloroform phase, after concentration, is dissolved in methanol/acetone, and is preferably passed through a RPLC column in order to remove the undesired lipid components which remain on the column, while taxanes are eluted from the column. This precolumn treatment obviates the need for the above indicated partition using ligroin, and provides for a simple and more convenient alternative to the ligroin treatment. The eluate is concentrated and can be chromatographed on a RPLC column as a suspension, e.g., in 20–30% acetonitrile/water.

If the needles of *Taxus floridana* are extracted and processed as described above, 10-deacetylbaccatin III, baccatin VI, and taxol result. The needles of *Taxus floridana* appear to be superior to the *Taxus brevifolia* as a Taxus source in terms of the isolated yields of taxanes.

Interestingly, 10-deacetylbaccatin III is found in the leaves of *Taxus baccata L* and can be extracted in fairly high yields (0.03% yield is reported in Jean-Noel Denis, et al., J. Am. Chem. Soc., 110:5817, 1988). Jean-Noel Denis, et al., ibid, describe the synthesis of taxol from 10-deacetylbaccatin (III) through a series of chemical transformations. Since 10-deacetylbaccatin III is more readily available from a natural source than taxol itself and the yew leaves from which the compound can be isolated are regenerated quickly, 10-deacetylbaccatin III can be used as a potential precursor of taxol.

Fractions containing taxanes collected from RPLC, on standing for several days, crystallize out the taxane derivatives of high purity. By contrast, fractions obtained using a silica gel column or a Florisil column pursuant to the prior art would not crystallize any taxane derivatives.

The isolation and purification method of this invention permits a highly efficient recovery of taxane derivatives in pure form from a naturally occurring Taxus species. The improvement with this invention over the prior art is reflected in the high overall recovery yield of the taxanes, e.g., 0.02-0.06% in the case of taxol as opposed to about 0.01% in the prior art, as well as in the purity of the taxanes isolated. Several other notable advantages associated with this invention are that: the reverse phase column employed has a very high capacity in terms of the ratio of silica to sample; the reverse phase column can be used repetitively, unlike a normal silica gel or Florisil column; and the reverse phase column allows the separation of taxanes with varying polarity, while polar taxanes tend to be adsorbed on a silica or Florisil column. Particularly, it is possible to use almost 3-10:1 ratio of the packing reverse phase silica to the sample amount charged on column. This compares very favorably with the 85:1 ratio obtained when using a Florisil column. Additionally, the second aspect is reflected in an economic advantage of this invention over the prior art.

Accordingly, this invention provides an attractive solution to the serious supply problem of taxol by furnishing high quantities of taxol and taxane derivatives which can be chemically transformed to taxol.

The invention will be described in further detail below by way of the embodiments thereof, but these embodiments should not be taken as limiting the scope of the invention. In the following examples, all concentrations are expressed as weight percent unless otherwise indicated.

EXAMPLE 1

The dried ground bark (1 kg) of *Taxus brevifolia* was extracted three to five times by percolation with 95% ethanol. The ethanol extract was concentrated at reduced pressure (15-25 mm at 35°-48° C.) to a brown syrup concentrate and partitioned between 1 L of water and 1 L of chloroform. After equilibration, the chloroform phase was separated and the aqueous phase was extracted twice with chloroform. The combined chloroform extract was dried over sodium sulfate and concentrated at reduced pressure to dryness, a solid material (15 g) was obtained.

The extracted solids were chromatographed on a preparative scale (38×300 mm) reversed phase $C_{18}$ column. The column was packed with about 100 g of $C_{18}$-silica. The elutant was a gradient of acetonitrile in water (e.g., 20, 25, 30, 35, 40, 45, 55, and 80% acetonitrile), at a flow rate of 6-12 ml per minute. Elution of peaks was monitored at 275 nm or by thin layer chromatography (silica plates, 5-10% methanol in chloroform; visualization by uv light as well as spray with 0.1-1.0N $H_2SO_4$ followed by gentle heating on a hot plate) and by analytical HPLC ($C_{18}$-silica, 40-50% acetonitrile in water as the eluant at 1 ml per minute).

A 10 g sample of the solid was dissolved in 10 ml-15 ml of acetonitrile and the solution diluted with 50 ml water at 45°-55° C. to give a 20-30% acetonitrile suspension. The resulting milky solution was applied to the column. The column was first eluted with 20% acetonitrile in water in 50-70 fractions of 15-20 ml each. After these fractions were collected, the column was eluted with an increasing concentration of acetonitrile in water in 100 fractions of 15-20 ml each.

Finally, the column was eluted with 80% acetonitrile in water and washed with a mixture of methanol, ethyl acetate, and ligroin (50:25:25). The column was reequilibrated with acetonitrile/water (1:4) for reuse.

Fractions 1-15 were combined and concentrated to dryness to yield a mixture of taxanes. Fractions 16-28 on concentration and trituration of the solid with 30-50% acetonitrile-water gave a crystalline solid which was filtered and recrystallized from acetone-hexane (1:1) to give a colorless, crystalline solid identified as 10-deacetylbaccatin III, yield 0.3 g, m.p. 232°-234° C.

IR (KBr): 3470, 3430, 1716 $cm^{-1}$.

NMR ($CDCl_3$/DMSO): 1.00 (S, 6H), 1.63 (S, 3H), 1.95 (S, 3H), 2.24 (S, 3H), 3.83 (d, J=7Hz, 1H), 4.47 (d, J=3Hz, 1H), 5.18 (d, J=3Hz, 1H), 5.44 (d, J=7Hz, 1H), 7.51 (d, J=7Hz, 3H), 8.01 (d, J=7Hz, 2H).

Elemental Analysis calculated for $C_{29}H_{36}O_{10}$: C, 63.96; H, 6.66%. Found: C, 63.82; H, 6.59%.

Fractions 40-50 on concentration gave a taxane identified as 10-deacetylcephalomannine-7-xyloside, yield 0.1 g, m.p. 250-252 (dec.).

IR(KBr): 3420, 2930, 1740-1710, 1660, 1600, 1585 $cm^{-1}$.

NMR($CDCl_3$): 0.857 (s, 3H), 1.122 (s, 3H), 1.177 (s, 3H), 1.262 (br.s, 6H), 1.577 (m, 1H), 1.740 (s, 3H), 1.899 (s, 3H), 2.174-2.255 (m, 2H), 2.363 (m, 3H), 2.580-2.676 (m, 1H), 3.015 (t, 1H), 3.162 (d, 1H), 3.320 (t, 1H), 3.795-3.855 (m, 1H), 4.057-4.293 (m, 2H), 4.545, 4.557 (d, 1H), 4.906, 4.936 (d, 1H), 5.330 (s, 1H), 5.461-5.502 (dd, 1H), 6.126 (t, 1H), 7.271-7.379 (m, 1H), 7.364, 7.379 (d, 4H), 7.499-7.689 (m, 5H), 7.864, 7.894 (d, 1H), 8.069 (d, 2H).

Elemental Analysis calculated for $Chd48H_{59}NO_{17}$.$H_2O$: C, 61.54; H, 6.50; N, 1.46%. Found: C, 61.62; H, 7.05; N, 1.42%.

Fractions 60-75 on concentration gave a taxane identified as 10-deacetyltaxol-7-xyloside, yield 1 g, m.p. 245°-248° C., optical rotation $-1°$ (in pyridine).

IR (KBr): 3540, 3420, 1750, 1720, 1710, 1645, 1600, 1580 $cm^{-1}$.

NMR(DMSO): 1.123 (s, 3H), 1.180 (s, 3H), 1.205-1.259 (m, 2H), 1.582 (m, 1H), 1.691 (m, 1H), 1.780 (s, 6H), 1.895 (s, 3H), 1.944-2.028 (m, 2H), 3.0-3.212 (m, DMSO), 3.513 (m, 1H), 3.594 (br. s, 1H), 3.836-3.850 (d, 2H), 3.870, 3.891 (d, 1H), 4.075, 4.098 (m, 1H), 4.135, 4.201 (m, 1H), 4.221-4.283 (m, 2H), 4.511-4.603 (br. m. 1H), 4.620, 4.713 (d, 1H), 4.924, 4.956 (d, 1H), 5.305 (s, 1H), 5.518-5.543 (m, 1H), 5.624, 5.849 (d, 2H), 5.743, 5.765 (br. d, 1H), 6.166, 6.194, 6.223 (t, 1H), 7.268, 7.281, 7.316 (m, 1H), 7.364-7.409 (m, 4H), 7.493-7.542 (m, 5H), 7.587, 7.811, 7.635 (m, 2H), 7.844, 7.869 (d, 2H), 8.102-8.193 (m, 2H), 8.163, 8.183 (d, 1H).

$^{13}$CNMR: 10.406, 13.546, 20.655, 22.314, 26.620, 34.805, 34.955, 38.677, 38.958, 39.235, 39.511, 39.760, 40.068, 40.343, 42.843, 46.209, 55.669, 56.221, 56.887, 57.106, 57.219, 60.747, 61.635, 61.733, 62.130, 63.201, 65.658, 66.429, 69.093, 69.819,. 73.115, 73.545, 74.150, 74.479, 75.265, 76.476, 76.853, 80.072, 80.659, 83.217, 102.898, 102.948, 102.997, 103.173, 103.249, 104.627, 127.019, 127.280, 128.124, 128.527, 129.434, 129.942, 131.169, 133.229, 134.419, 136.053, 136.383, 139.241, 165.137, 166.169, 169.774, 172.548, 208.196.

Elemental Analysis calculated for $C_{51}H_{57}NO_{17} \cdot H_2O$: C, 62.88; H, 6.10; N, 1.43%. Found: C, 62.94; H, 6.02; N, 1.58%.

The m.p., optical rotation and $^1$Hnmr spectra agreed with those reported by V. Senilh, et al., J. Nat. Prod. 47, 131 (1984).

Fractions 85–90 on concentration gave a taxane identified as brevitaxane A, yield 0.1 g, m.p. 220°–222° C., optical rotation −27° C. (in chloroform).

IR(KBr): 3570, 3400, 2980, 2930, 1740–1730, 1655, 1590 cm$^{-1}$.

NMR(CDCl$_3$): 0.899 (s, 3H), 1.039 (s, 3H), 1.267 (m, 1H), 1.343 (s, 3H), 1.50 (d, 1H), 1.743 (s, 3H), 1.87 (m, 1H), 2.008 (s, 3H), 2.075 (s, 3H), 2.318 (m, 1H), 2.466 (m, 1H), 2.677 (s, 1H), 2.746 (d, 1H), 4.380 (br. s, 1H), 4.440 (s, 1H), 4.690 (br. s, 1H), 4.823 (s, 1H), 5.180 (s, 1H), 5.565 (dd, 1H), 6.06 (d, 1H), 6.522 (d, 1H), 7.429 (m, 2H), 7.554 (m, 1H), 7.861 (d, 2H).

$^{13}$C NMR (DMSO): 11.727, 11.957, 20.559, 21.258, 26.405, 27.088, 28.008, 36.511, 38.846, 44.652, 46.657, 61.168, 69.283, 69, 594, 70.639, 74.663, 75.165, 77.291, 109.690, 1128.677, 129.222, 129.771, 133.221, 134.001, 150.311, 151.271, 164.138, 169.162, 169.337.

Elemental Analysis calculated for $C_{31}H_{40}O_9$:C, 66.89; H, 7.24%. Found: C, 67.13; H, 7.35%.

Fractions 100–115 on concentration gave a taxane identified as 10-deacetyltaxol, yield 1.0 g, m.p. 192°–196° C.

IR(KBr): 3430, 2920, 2840, 1740-1710, 1650, 1600, 1575, 1520 cm$^{-1}$.

NMR (CDCls): 1.10 (s, 3H), 1.19 (s, 3H), 1.42 (s, 3H), 1.74 (s, 3H), 1.872 (m, 1H), 2.275 (m, 1H), 2.375 (s, 3H), 2.5 (m, 1H), 3.74, 3.76 (d, 1H), 3.868, 3.891 (d, 1H), 4.18-4.315 (m, 2H), 4.77 (dd, 1H), 4.93 (d, 1H), 5.18 (s, 1H), 5.67 (d, 1H), 5.76 (dd, 1H), 6.176 (t, 1H), 7.16 (d, 1H), 7.388-7.529 (m, 9H), 7.76, 7.784 (d, 2H), 8.099, 8.125 (d, 2H).

$^{13}$C NMR (CDCl$_3$): 9.907, 14.307, 20,656, 22.581, 26.614, 26.969, 36.061, 37.070, 43.114, 46.556, 55.116, 57.791, 72.026, 72.466, 73.336, 74.580, 74.951, 78.854, 81.231, 84.178, 127.079, 128.310, 128.693, 128.716, 128.975, 129.324, 130.195, 130.259, 1 31.898, 133.663, 133.817, 138.054, 138.112, 166.978, 167.019, 170.439, 172.544, 211.270.

Fractions 120–130 on concentration gave a taxane identified as taxol-7-xyloside, yield 0.1 g, m.p. 236°–238° C.

IR (KBr): 3400, 1740, 1650, 1590, 1520 cm$^{-1}$.

NMR (CDCl$_{13}$): 1.2 (s, 6H), 1.76 (s, 3H), 1.85 (s, 3H), 2.15 (m, 1H), 2.22 (s, 3H), 2.75 (m, 2H), 3.27 (br. s., 2H), 3.63 (m, 2H), 3.84 (m, 2H), 4.21 (br. s., 2H), 4.32 (m, 2H), 4.79 (s, 1H), 4.90 (d, 1H), 5.68 (d, 1H), 5.79 (d, 1H), 6.10 (t, 1H), 6.38 (s, 1H), 7.03 (d, 1H), 7.40-7.60 (m, 11H), 7.74 (d, 2H), 8.12 (d, 2H). $^{13}$CNMR (CDCl$_3$): 11.02, 14.60, 21.04, 22.65, 26.50, 35.24, 35.70, 43.20, 46.76, 55.09, 57.81, 64.40, 69.32, 72.11, 72.19, 73.25, 74.63, 76.08, 76.77, 77.10, 77.61, 78.62, 79.34, 81.29, 83.86, 127.07, 128.34, 128.70, 129.00, 130.19, 131.93, 133.80, 133.72, 138.07, 140.03, 166.92, 167.09, 170.59, 172.61, 201.98.

Fractions 160–165 on concentration gave a solid which was recrystallized twice from acetonitrile/water (1:1) to give cephalomannine, yield 0.04 g, m.p. 184°–186° C.

Identification of cephalomannine was carried out by comparison between chromatographic characteristics (TLC, HPLC) of the sample thus obtained and those of an authentic sample, as well as by other spectroscopic comparison, i.e., IR, NMR, OR, etc.

Fractions 175–195 when similarly concentrated and the solid recrystallized twice from acetonitrile/water (1:1) gave taxol as a colorless, crystalline solid, yield 0.4 g, m.p. 212°–214° C., optical rotation −49°, (1% in chloroform).

IR (KBr): 3450 (broad), 1730, 1710, 1650 cm$^{-1}$.

NMR (CDCl$_3$/DMSO): 1.18 (S, 6H), 1.64 (S, 3H), 1.89 (S, 3H), 2.17 (S, 3H), 2.38 (S, 3H), 3.80 (t, 1H), 4.66 (m, 1H), 4.90 (d, 1H), 5.65 (t, 1H) 6.19 (m, 1H), 6.28 (S, 1H), 7.22–8.24 (m, 15H).

Elemental Analysis calculated for $C_{47}H_{51}NO_{14}$: C, 66.10; H, 6.02; N, 1.64%. Found: C, 66.21; H, 6.04; N, 1.63%.

Mother liquors from the recrystallization of 10-deacetylbaccatin III were rechromatographed on RP C-8 column using 20–30% acetonitrile/water and increasing to 40–50% acetonitrile/water. Fractions containing the major peak corresponding to 10-deacetylbaccatin III were combined, concentrated and the solid recrystallized as before to give an additional 0.1 g for a total yield of 0.4 g (0.04% yield, based on plant material).

Mother liquors from taxol recrystallization and cephalomannine recrystallization were concentrated together with the original column fractions beyond 195 and the material rechromatographed using RP C$_8$ silica using 40–50% acetonitrile in water. The taxol-containing fractions were concentrated and the solid recrystallized from 1:1 acetonitrile/water to give an additional 0.1 g of taxol for a total yield of 0.5 g (0.05% yield, based on plant material).

FIG. 1 outlines the above isolation procedure and the mass balance achievable therefrom.

EXAMPLE 2

The dried needles (1 kg) of *Taxus brevifolia* was extracted three times by percolation with methanol. The methanol extract was concentrated at reduced pressure (15–25 mm at 35°–45° C.) to a dark green syrup concentrate. The concentrate was partitioned between 1 L of 4:1 methanol/water and 1 L of ligroin. The aqueous methanol phase was diluted with water (1 L) and extracted first with benzene (twice) and then with chloroform. The benzene extract was dried over sodium sulfate and concentrated at reduced pressure to dryness. The solid material (8 g) was thus obtained.

The solid was chromatographed as described under Example 1 except that RPLC C$_8$ silica (100 g) was used in methanol/water 20%. A pressure of 50 psi was used to obtain an adequate rate. One hundred fifty fractions of 10 ml were collected, while a gradient of 25, 35, 45, 55 and 65% methanol in water was being used. The fractions were monitored as before and fractions containing 10-deacetylbaccatin III (fractions 25-35), brevitaxane A (fractions 60-90), cephalomannine (fractions 120-125) and taxol (fractions 135-150) were combined separately, concentrated to dryness and recrystallized from chloroform/hexane (1:1) to give the pure compounds. 10-deacetylbaccatin III, brevitaxane A, 2.0 g (0.2% yield, based on plant material), cephalomannine, 0.03 g (0.003% yield, based on plant material) and taxol 0.1 g (0.01% yield, based on plant material).

The chloroform extract solids (10 g) were likewise chromatographed on RPLC $C_8$ silica using 20% methanol/water which was raised to 65% methanol/water. Fractions containing 10-deacetylbaccatin III were concentrated and the product crystallized as before to yield an additional amount of 10-deacetylbaccatin III, providing a total combined yield of 0.2 g (0.02% yield, based on plant material).

Figure 2:
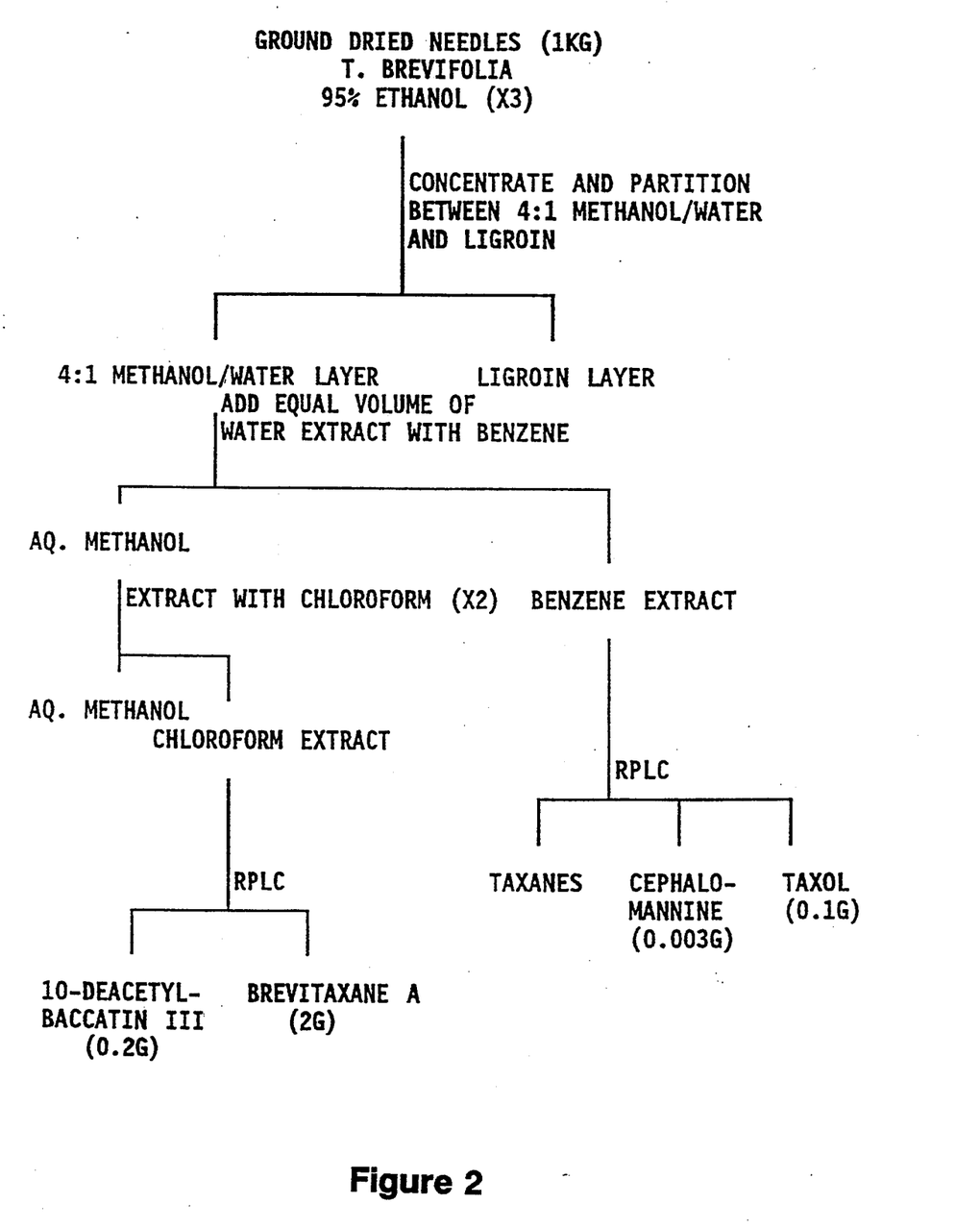
FIG. 2 shows another separation scheme for isolating taxanes from *Taxus brevifolia* in accordance with this invention.

FIG. 2 outlines the above isolation procedure and the mass balance achievable therefrom.

EXAMPLE 3

The extraction procedure of EXAMPLE 2 was repeated, except that the aqueous methanol extract was further extracted with chloroform. The chloroform extract was dried over sodium sulfate and concentrated at reduced pressure to dryness. The solid obtained (10 g) was chromatographed on RPLC CN-bonded silica (150 g) in acetonitrile/water 30–40% using substantially the same conditions as those described in EXAMPLE 1. Fractions containing 10-deacetylbaccatin III, brevitaxane A, cephalomannine and taxol were separately collected and the four compounds isolated. The yields were approximately the same as those given in EXAMPLE 2.

EXAMPLE 4

The methanol extract (from approximately 90 lbs. of the needles of *T. brevifolia*) obtained according to the procedure of Example 2 was partitioned between 10 L of water and 10 L of chloroform. After two more extractions with chloroform, the combined chloroform extracts were concentrated to yield a dark green viscous mass (1200 g). Of this, 250 g was dissolved in 70–80% methanol and 5–10% acetone (total 1l) to make a 25% solution. This solution was passed through an RP-$C_{18}$ column (app. 500 g of the adsorbent), equilbrated in the same solvent mixture. Nearly all of chlorophylls and waxes (which account for app. 50% of the total weight) remained on the column while taxanes were eluted.

The eluate containing the taxanes was concentrated to near dryness and the resulting solid (110 g) was dissolved in 20–25% acetonitrile/water (500–600 ml) and applied to a RP-$C_{18}$ column (500 g). The column was eluted with increasing concentrations of acetonitrile in water (e.g., a step gradient: 25, 30, 35, 40, 45, 60% acetonitrile in water) and taxol, 10-deacetylbaccatin III, brevitaxane A, and cephalomannine were isolated with the yields of respective compounds being substantially the same as those given in EXAMPLE 2.

EXAMPLE 5

Approximately 10 kg of the needles and small twigs (<0.5" diameter) of *T. floridana* were extracted as described in Example 2. The methanol extract was partitioned between water (3 L) and chloroform (3 L). After two more extractions with chloroform (2 L each), the combined chloroform extract was concentrated to a thick green syrup (220 g). The sample was dissolved in a mixture of methanol, acetone and water (70–80, 5–10 and 20) and the solution passed through a column of RP-C18 column made from 500 g of the adsorbent. The column was washed with the same solvent mixture until the uv absorbance indicated that washing was complete. The effluent and the wash were concentrated to near dryness and the residue (app. 100 g) taken up in 20–30% acetonitrile/water (500–600 ml) and applied to a column of RPLC $C_8$ from app. 500 g of the adsorbent. A step gradient was set up as before. Fractions of 200 ml were collected and monitored as before. On standing, the various fractions began to crystallize. After one week the fractions containing the various components: 10-deacetylbaccatin III, baccatin VI, cephalomannine and taxol were filtered and the respective solids recrystallized. The mother liquors from each of these were separately chromatographed on small columns of silica gel and additional quantities of the components isolated. 10-deacetylbaccatin III, 0.05%, baccatin VI, 0.02% and taxol, 0.01%.

Baccatin VI had the following physical properties: m.p. 246°–251° C.; (lit. 244°–245° C. D. P. Della Casa de Marcano, et al., J. Chem. Comm., 365, 1975).

$^{13}C$ NMR (DMSO): 12.404, 14.267, 20.440, 20.569, 21.067, 22.434, 27.944, 34.215, 35.085, 42.743, 45.136, 46.409, 69.164, 70.035, 71.218, 72.623, 74.216, 75.267, 76.581, 80.598, 82.827, 128.629, 129.671, 129.736, 233.334, 133.847, 165.153, 168.731, 169.401, 169.473, 170.147, 170.435.

Figure 3:
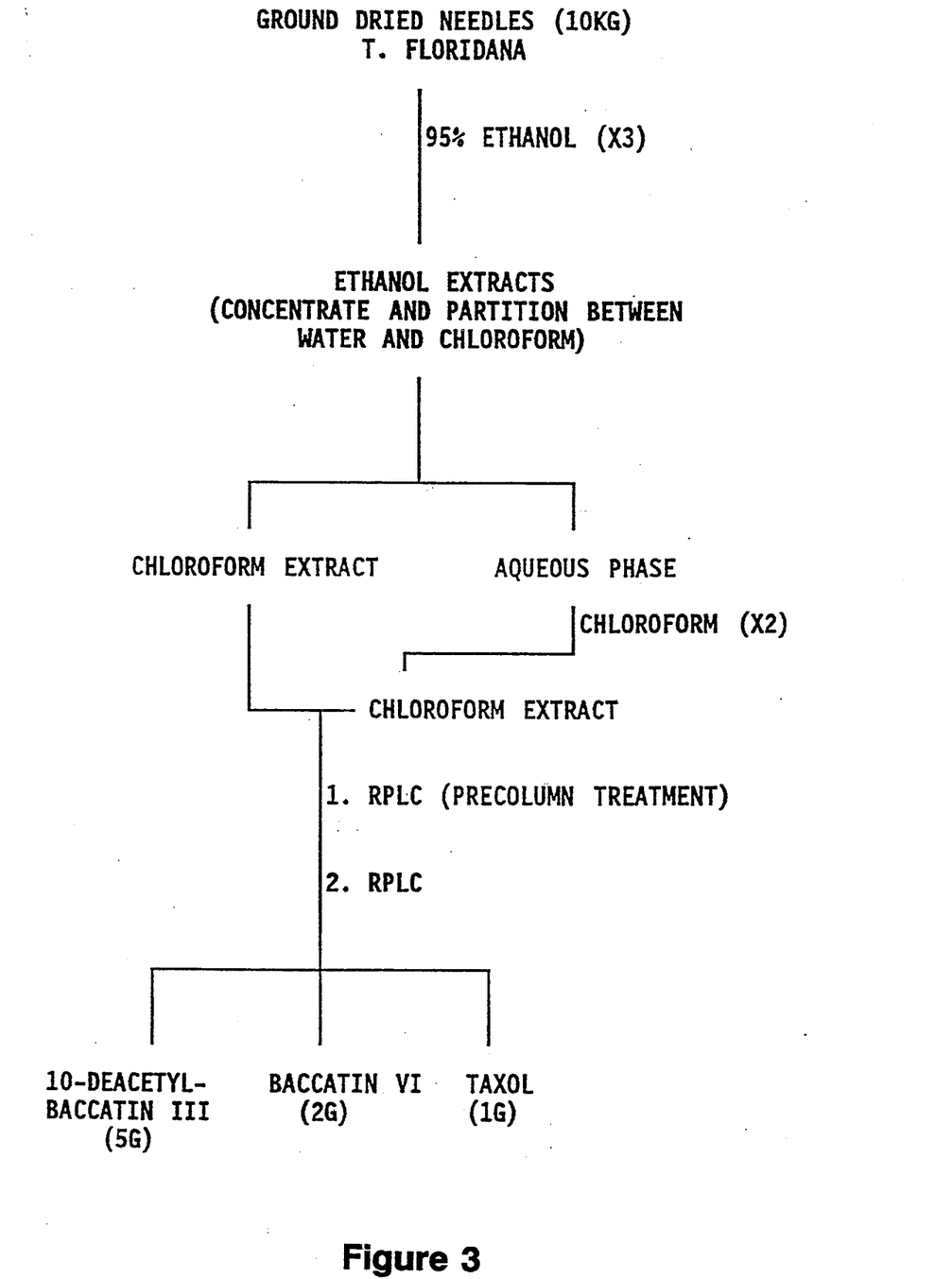
FIG. 3 shows a further separation scheme for isolating taxanes from *Taxus floridana* in accordance with this invention.

FIG. 3 outlines the above isolation procedure and the mass balance achievable therefrom.

The invention now being fully described, it will be apparent to one of ordinary skill in the art that many changes and modifications can be made without departing from the spirit or scope of the invention.

I claim:

1. A taxane having the following structure:

* * * * *

UNITED STATES PATENT AND TRADEMARK OFFICE
CERTIFICATE OF CORRECTION

PATENT NO.  :  5,380,916

DATED  :  January 10, 1995

INVENTOR(S)  :  Koppaka V. Rao

It is certified that error appears in the above-identified patent and that said Letters Patent is hereby corrected as shown below:

Title Page: "[22] PCT Filed: Nov. 4, 1901" should read --[22] PCT Filed: Nov. 4, 1991--; "*Assistant Examiner*"—Deborah Lambrin" should read -- *Assistant Examiner*—Deborah Lambkin--; [57] ABSTRACT, line 9: "deacetyitaxol" should read --deacetyltaxol--.

Column 1:  lines 23-36:

should read

UNITED STATES PATENT AND TRADEMARK OFFICE
CERTIFICATE OF CORRECTION

PATENT NO.   :   5,380,916

DATED        :   January 10, 1995

INVENTOR(S)  :   Koppaka V. Rao

It is certified that error appears in the above-identified patent and that said Letters Patent is hereby corrected as shown below:

UNITED STATES PATENT AND TRADEMARK OFFICE
CERTIFICATE OF CORRECTION

PATENT NO. : 5,380,916

DATED : January 10, 1995

INVENTOR(S) : Koppaka V. Rao

It is certified that error appears in the above-identified patent and that said Letters Patent is hereby corrected as shown below:

Columns 5-6: Brevitaxane A:

should read

Column 6: line 43: "alcohol. acetone" should read --alcohol, acetone--.
Column 7: line 23: "/minute. whereas" should read --/minute, whereas--.
Column 10: line 43: "Chd48H$_{59}$" should read --C$_{48}$H$_{59}$--; line 44: "1.46%" should read --1.48%--.

UNITED STATES PATENT AND TRADEMARK OFFICE
CERTIFICATE OF CORRECTION

PATENT NO.    :    5,380,916

DATED         :    January 10, 1995

INVENTOR(S)   :    Koppaka V. Rao

It is certified that error appears in the above-identified patent and that said Letters Patent is hereby corrected as shown below:

Column 11:  line 24: "38.846" should read --38.848--; line 35: "(CDCl$_S$)" should read --(CDCl$_3$)--; line 44: "72.466" should read --72.486--; line 46: "1 31.898" should read --131.898--.

Signed and Sealed this

Eleventh Day of April, 1995

*Attest:*

BRUCE LEHMAN

*Attesting Officer*    *Commissioner of Patents and Trademarks*